United States Patent [19]

Reiter et al.

[11] Patent Number: 5,153,353

[45] Date of Patent: Oct. 6, 1992

[54] P-OXYBENZOIC ACID DERIVATIVES, PROCESS FOR THE PREPARATION THEREOF AND USE THEREOF AS DRUG

[75] Inventors: Friedemann Reiter, Putzbrunn; Peter Jank, Hofolding; Michael Schliack, Munich; Kaisli Kaipainen-Reiter, Putzbrunn; Gerhard Lang, Freising; Anke Schink, Grasbrunn, all of Fed. Rep. of Germany

[73] Assignee: Klinge Pharma GmbH, Munich, Fed. Rep. of Germany

[21] Appl. No.: 742,600

[22] Filed: Aug. 8, 1991

[30] Foreign Application Priority Data

Oct. 9, 1990 [DE] Fed. Rep. of Germany ....... 4032037

[51] Int. Cl.$^5$ .................... C07C 69/76; C07C 65/00
[52] U.S. Cl. .................. 560/64; 562/473; 560/55
[58] Field of Search ............. 560/64; 562/473; 514/532, 533, 544, 568

[56] References Cited

U.S. PATENT DOCUMENTS

| | | | |
|---|---|---|---|
| 4,073,935 | 12/1975 | Grill et al. | 424/308 |
| 4,109,013 | 11/1977 | Grill et al. | 424/315 |
| 4,144,351 | 11/1977 | Grill et al. | 424/278 |
| 4,189,594 | 8/1978 | Grill et al. | 560/53 |
| 4,582,857 | 7/1984 | Grill et al. | 562/463 |

FOREIGN PATENT DOCUMENTS

| | | |
|---|---|---|
| 133935 | 7/1984 | European Pat. Off. |
| 2460689 | 7/1976 | Fed. Rep. of Germany |
| 2735856 | 2/1979 | Fed. Rep. of Germany |
| 3326164 | 1/1985 | Fed. Rep. of Germany |

*Primary Examiner*—Paul J. Killos
*Attorney, Agent, or Firm*—Brumbaugh, Graves, Donohue & Raymond

[57] ABSTRACT p-Oxybenzoic acid derivatives of the general formula (1)

wherein:

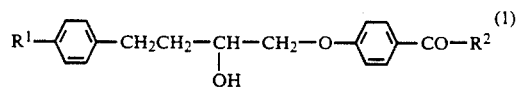

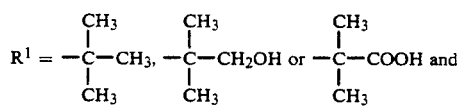

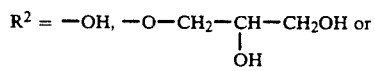

where in the case of

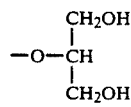

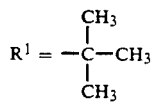

and in the case of

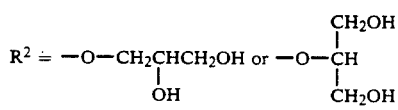

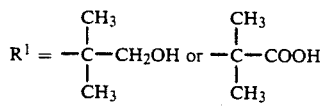

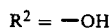

their physiologically compatible salts and their enantiomeric and diastereomeric forms have hypolipemic properties and are therefore suitable for the preparation of drugs with hypolipemic action.

7 Claims, No Drawings

P-OXYBENZOIC ACID DERIVATIVES, PROCESS FOR THE PREPARATION THEREOF AND USE THEREOF AS DRUG

DE-OS 3,326,164 and European patent 0 133 935 disclose therapeutically valuable p-oxybenzoic acid derivatives of the general formula

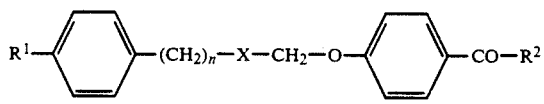

wherein:

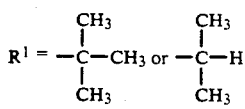

n = 1 or 2

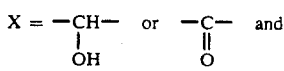

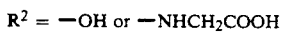

$R^2 = -OH$ or $-NHCH_2COOH$ and their physiologically compatible salts

From DE-OS 3,326,164 and European patent 0 133 935 processes are further known for the preparation of the aforementioned compounds and their use for making a drug with hypolipemic effect.

It is also known that certain benzoic acids etherized in paraposition have hypolipemic properties, that is benzoic acid derivatives deriving from ethers of glycerol (DE-PS 2,460,689) or of 1,3-dihydroxyacetone (DE-OS 2,735,856).

It has now surprisingly been found that the advantageous pharmacodynamic and pharmacokinetic properties can become even more pronounced if in modification of the known compounds of DE-OS 3,326,164 other substitutents are used for $R^1$ and $R^2$.

The subject of the present invention is p-oxybenzoic acid derivatives of the general formula (1)

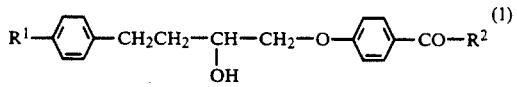

their physiological compatible salts, their enantiomers or diastereomers, where

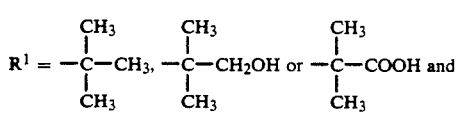

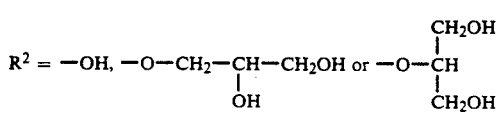

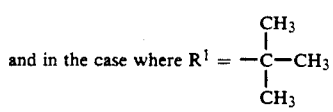

$R^2 = -OH$ is possible.

The subject of the invention is furthermore a process for the preparation of the compounds according to the invention which is characterized in that epoxides of the general formula (2)

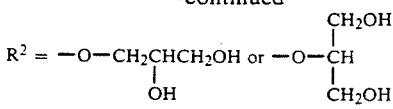

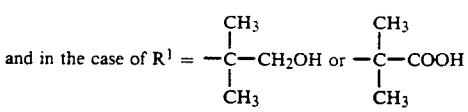

and both X and Y represent a suitable protective group, for example acetyl, are reacted with the corresponding p-hydroxybenzoic acid esters in the presence of alkali and the possibly present protective groups are split off. Methods may be used here as are known from DE-OS 3,326,164.

The following examples are intended to explain the invention in detail.

The compounds listed in the following table 1 have been detected:

TABLE 1

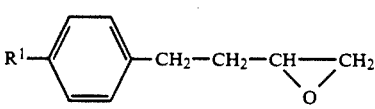

| Nr. | $R^1$ | $R^2$ |
|---|---|---|
| 1 | $(CH_3)_3C$ | $OCH_2CHCH_2OH$ <br> $\quad\quad\quad\;\; \vert$ <br> $\quad\quad\quad\;\; OH$ |
| 2 | $HOCH_2C(CH_3)_2$ | OH |
| 3 | $HOOCC(CH_3)_2$ | OH |

EXAMPLE 1

4-[4-(4'-tert. butylphenyl)-2-hydoxybutoxy]benzoic acid-2,3-dihydroxypropyl ester a) 4-[4-(4'-tert.butylphenyl)-2-hydroxybutoxy]benzoic acid-(2,2-dimethyl-1,3-dioxolane-4-yl)-methyl ester To the solution of 27.7 g (0.110 Mol) 4-hydroxybenzoic acid-(2,2-dimethyl-1,3-dioxolane-4-yl)-methyl ester in 200 ml absolute dimethyl formamide, 0.300 g (0.010 Mol) 80% sodium hydride is added at room temperature while stirring and after completion of the gas development 20.4 g (0.100 Mol) 4-(4'-tert.butyl phenyl)-1,2-epoxybutane. The mixture is heated for 20 hours to 100°-110° C. After cooling the reaction mixture it is poured into ice water, the solution acidified, the product absorbed in ethyl acetate and the organic phase washed with water. After drying over sodium sulfate the solvent is removed in vacuum. 47.2 g of a yellow brown viscous raw product is obtained which is used without purification for the further reaction.

$^1$H-NMR-Spectrum (CDCl$_3$):

| 1.31 | s | (9) | (CH$_3$)$_3$C |
|---|---|---|---|
| 1.39, 1.45 | 2s | (6) | (CH$_3$)$_2$C |
| 1.73 to 2.05 | m | (2) | ArCH$_2$CH$_2$ |
| 2.35 | d | (1) | OH |
| 2.57 to 3.00 | m | (2) | ArCH$_2$CH$_2$ |
| 3.70 to 4.23 | m | (5) | CH$_2$CHO, CH$_2$O |
| 4.27 to 4.53 | m | (3) | COOCH$_2$CH |
| 6.80 to 8.15 | m | (8) | Aromate |

NMR spectra taken at 100 MHz.

The chemical shifts are indicated in ppm against TMS ($\delta$=0.0) and the relative intensities are added in brackets. s=singlet; d=doublet; t=triplet; q=quartet; m=multiplet.

b) Preparation of 4-[4-(4'-tert.butyl phenyl)-2-hyroxy-butoxy]benzoic acid-2,3-dihydroxypropyl ester The solution of 47.2 g crude 4-[4-(4'-tert.butyl phenyl)-2-hydroxybutoxy]benzoic acid-(2,2-dimethyl-1,3-dioxolane-4-yl-methyl ester in 200 ml tetrahydrofuran is mixed with 35 ml 5M hydrochloric acid and stirred for two hours at room temperature. This is poured into ice water, the product absorbed in ethyl acetate and washed with water. After drying over sodium sulfate the solvent is removed in vacuum. The oily gradually crystallizing residue is recrystallized four times from ethyl acetate. Colourless crystals with melting point 101°–103° C.; yield 18.1 g (43%).

C$_{21}$H$_{32}$O$_6$(416.5)

Mole mass 416 (determined by mass spectrometry using electron impact ionization (70 eV))

| IR-Spectrum (KBr): | | | $\nu$(OH) | 3640–3120 cm$^{-1}$ |
|---|---|---|---|---|
| | | | $\nu$(C=O) | 1710 cm$^{-1}$ |
| $^1$H-NMR-Spectrum (CDCl$_3$): | | | | |
| 1.30 | s | (9) | (CH$_3$)$_3$C | |
| 1.75 to 2.04 | m | (2) | ArCH$_2$CH$_2$ | |
| 2.63 to 3.10 | m | (4) | ArCH$_2$CH$_2$, 2OH | |
| 3.50 | d | (1) | OH | |
| 3.57 to 4.20 | m | (6) | 2CH$_2$CHO | |
| 4,35 | d | (2) | COOCH$_2$ | |
| 6.70 to 8.03 | m | (8) | Aromate | |

EXAMPLE 2

4-{4-[4'-(2-hydroxy-1,1-dimethylethyl)phenyl]-2-hydroxybuty} benzoic acid a)
4-[4-{4'-[1,1-dimethyl-2-(tetrahydropyran-2-yl)oxyethyl]phenyl}-2-hydroxybutoxy-benzoic acid methyl ester 30.4 g (0.100 Mol) 4-{4'-[1,1-dimethyl-2-(tetrahydropyran-2-yl)oxyethyl]phenyl}-1,2-epoxy butane, 15.2 g (0.100 Mol) 4-hydroxybenzoic acid methyl ester and 1.74 g (0.010 Mol) 4-hydroxy benzoic acid methyl ester sodium salt are heated in 100 ml dimethyl formamide for 23 hours while stirring to 100°–110° C. The cooled reaction mixture is poured into water, the precipitating product taken up in ethyl acetate and the organic phase washed with water. After drying over sodium sulfate the solvent is removed in vacuum and the residue chromatographed on silica with dichloromethane/methanol 99/1. A highly viscous oil is obtained; yield 32.5 g (71%).

| $^1$H-NMR-Spectrum (CDCl$_3$), (60 MHz): | | | |
|---|---|---|---|
| 1.13 bis 2.27 | m | (14) | (CH$_3$)$_2$C, (CH$_2$)$_3$, ArCH$_2$CH$_2$ |
| 2.50 bis 3.03 | m | (3) | ArCH$_2$CH$_2$, OH |
| 3.77 bis 4.33 | m | (10) | CH$_2$CHO, 2CH$_2$O, CH$_3$O |
| 4.50 | wide s | (1) | OCHO |
| 6.67 to 8.10 | m | (8) | Aromate | b)
4-[4-{4'-[1,1-dimethyl-2-(tetrahydropyran-2-yl)oxyethyl]phenyl}-2-hydroxybutoxy]benzoic acid ester 32.5 g (0.071 Mol) 4- 4-4'- 1,1-dimethyl-2-(tetrahydropyran-2-yl)oxyethyl phenyl-2-hydroxybutoxy benzoic acid methyl ester in 130 ml methanol are mixed with a solution of 16.0 g (0.230 Mol) potassium hydroxide in 55 ml water and heated under reflux for 3 hours. Thereafter the solvent is removed in vacuum, the residue taken up in water and extracted with ether and the aqueous phase acidified with concentrated hydrochloric acid. The precipitating product is taken up in ethyl acetate and the organic phase washed with water. After drying over sodium sulfate the solvent is removed in vacuum. 31.2 g yellow resin is obtained as residue (raw yield 99%).

c) Manufacture of 4-{4-[4'-(2-hydroxy-1,1-dimethylethlphenyl]-2-hydroxybutoxy}-benzoic acid 31.2 g (0.070 Mol) 4-[4-{4'-1,1-dimethyl-2-(tetrahydropyran-2-yl)oxyethyl]phenyl}-2-hydroxybutoxybenzoic acid are disolved in 100 ml methanol and stirred with 10 ml concentrated hydrochloric acid for 1 hour at 40°–50° C. Dilution is then carried out with water, the precipitating product taken up in ethyl acetate and the organic phase washed with water. After drying over sodium sulfate the solvent is removed in vacuum and the residue recrystallized three times from acetonitrile/trichloromethane (9/1). Colourless crystals with melting point 118°–119° C.; yield 13.0 g (52%).

C$_{21}$H$_{26}$O$_5$(358.4)

Mass spectrum: m/e=327 (100%) (M+—CH$_2$OH) (no M+)

| IR-Spectrum (KBr): | | | $\nu$(OH) | 3600–2400 cm$^{-1}$ |
|---|---|---|---|---|
| | | | $\nu$(C=O) | 1675 cm$^{-1}$ |
| $^1$H-NMR-Spectrum (CDCl$_3$): | | | | |
| 1.31 | s | (6) | (CH$_3$)$_2$C | |
| 1.75 to 2.10 | m | (2) | ArCH$_2$CH$_2$ | |
| 2.58 to 2.97 | m | (2) | ArCH$_2$CH$_2$ | |
| 3.58 | s | (2) | CH$_2$OH | |
| 3.82 to 4.30 | m | (6) | CH$_2$CHO, 3OH | |
| 6.77 to 8.10 | m | (8) | Aromate | |

EXAMPLE 3

4-{4-[4'-(1-carboxy-1-methylethyl)phenyl]-2-hydroxybutoxy}benzoic acid a) 4-{4-[4'-(methoxy carbonyl-1-methylethyl)phenyl]-2-hydroxybutoxy}-benzoic acid methyl ester 24.8 g (0.100 Mol) 4- [4'-(1-methoxy carbonyl-1-methylethyl)-phenyl]- 1,2-epoxybutane, 15.2 g (0.100 Mol) 4-hydroxybenzoic acid methyl ester and 1.74 g (0.010 Mol) 4-hydroxy-benzoic acid methyl ester sodium salt are stirred in 100 ml dimethyl formamide for 12 hours at 100°–110° C. The cooled reaction mixture is poured into water, the precipitating product taken up in ethyl acetate and the organic phase washed with water. After drying over sodium sulfate the solvent is removed in vacuum and the residue (3.91 g, raw yield 98%) further reacted without purification.

| $^1$H-NMR-Spectrum (CDCl$_3$) (60 MHz): | | | |
|---|---|---|---|
| 1.57 | s | (6) | (CH$_3$)$_2$C |
| 1.73 to 2.20 | m | (2) | ArCH$_2$CH$_2$ |
| 2.50 to 3.20 | m | (3) | ArCH$_2$CH$_2$, OH |
| 3.63 | s | (3) | OCH$_3$ |
| 3.70 to 4.20 | m | (6) | CH$_2$CHO, CH$_3$O |
| 6.63 to 8.10 | m | (8) | Aromate | b) Manufacture of 4-{4-[4'-(1-carboxy-1-methylethyl)phenyl]-2-hydroxybutoxy}-benzoic acid 39.1 g (0.098 Mol) crude 4-{4-[4'(1-methoxy carbonyl-1-methylethyl)phenyl]-2-hydr oxybutoxy}benzoic acid methyl ester in 150 ml methanol is mixed with a solution of 30 g (0.440 Mol) potassium hydroxide in 40 ml water and stirred overnight at room temperature. This is then poured into water, the solution extracted with tert. butylmethyl ether and the aqueous solution acidified with concentrated hydrochloric acid. The precipitating product is taken up in ethyl acetate and the organic phase washed with water. After drying over sodium sulfate the solvent is removed in vacuum. The residue is recrystallized twice from acetonitrile with addition of methanol (5 vol. %) and then twice from acetonitrile/trichloromethane (2:1). Colourless crystals with a melting point of 152°–155° C.; yield 13.7 g (37%).

Mass spectrum: m/e=328 (15%), (M+—CO$_2$) (no M+)

| IR-Spectrum (KBr): | $\nu$(OH) | 3600–2300 cm$^{-1}$ | |
| | $\nu$(C=O) | 1690 cm$^{-1}$ | |
| $^1$H-NMR-Spectrum (CDCl$_3$/CD$_3$OD): | | | |
| 1.57 | s | (6) | (CH$_3$)$_2$C |
| 1.73 to 2.10 | m | (2) | ArCH$_2$CH$_2$ |
| 2.50 to 3.08 | m | (2) | ArCH$_2$CH$_2$ |
| 3.84 to 4.06 | m | (3) | CH$_2$CHO |
| 4.85 | wide s | (3) | 3OH |
| 6.80 to 8.10 | m | (8) | Aromate |

For the therapeutic use as hypolipemic drug the new compounds of the general formula (1) and their salts are preferably administered orally. Generally, the oral daily dose for adults is 0.1 to 5 g, preferably 0.3 to 2 g.

The active substances can be prepared for oral administration in the usual galenic manner. As pharmaceutical substrates common auxiliary substances are suitable, such as lactose, saccharose, mannite, potato starch or maize starch, cellulose derivatives or gelatins, possibly with addition of lubricants, for example magnesium or calcium stearate, and polyethylene glycols.

EXAMPLE 250 g of the compound of example 1 is mixed with 250 g polyethylene glycol and introduced by the Scherer method into one thousand soft gelatin capsules which each contained 250 mg active substance.

Preferred administration forms are hard capsules of hard gelatins and sealed soft capsules. In hard capsules, the pure active substance may possibly be contained with a small addition of lubricants. With corresponding physicochemical properties of the active substances processing to granulates is preferred and as auxiliary substances potato or maize starch, microcyrstalline cellulose, cellulose derivatives, gelatin or also highly dispersed silicic acids can be used.

In the manufacture in soft gelating capsules the pure active substance is dissolved or suspended in suitable liquids, for example in liquid polyethylene glycols or vegetable oils.

Pharmacodynamic effects of the compounds claimed

The superiority of the compounds claimed over the CLOFIBRAT already established for a long time in therapy can be clearly proved by the lipid-lowering effect.

1) Determination of the hypolipemic effect in rats

The lipid-lowering effect of the test substances was examined in groups each of 10 normolipemic, male Wister rats of 200 to 220 g in weight.

The investigations were performed after a 3-week adaption training of the eating habits of the animals. The controlled feeding was carried out daily from 8 a.m. to 10 a.m. The test substances were administered at 11 a.m.

The test compounds were absorbed in an aqueous solution of 0.25% agar and 0.84% NaCl and administered orally. After three administrations over a period of three days blood was extracted from the animals.

The determination of cholesterol and triglycerides in the serum was made with the aid of the "Cobas-Bio" centrifugal analyzer of Hoffmann-La Roche.

Methods:
a) Cholesterol determination CHOS-PAP method, enzymatic colour test according to J. Siedel et al. (J. Clin. Chem. Clin. Biochem. 19, 838 (1981))
b) Triglyceride determination Enzymatic cleavage of the triglycerides with the aid of specific lipases with subsequent determination of the liberated glycerol according to T. O. Tiffany et al. (Clin. Chem. 20, 476 (1974))

TABLE 2

Percentage change of the total cholesterol (TC) - and triglyceride (TG) - level in the rat serum after oral administration of the test substances

| Compound number Comparison substance | Dose (mg/kg) | % change TC $\overline{X} \pm$ SD | % change TG $\overline{X} \pm$ SD |
|---|---|---|---|
| CLOFIBRAT | 100 | −14.5 ± 12.0 | −29.2 ± 19.4 |
| 1 | 10 | +3.8 ± 16.4 | −26.2 ± 51.1 |
| 1 | 30 | −17.1 ± 13.9 | −28.5 ± 9.0 |
| 1 | 100 | −44.1 ± 10.8 | −34.7 ± 8.6 |

TABLE 2-continued

Percentage change of the total cholesterol (TC) - and triglyceride (TG) - level in the rat serum after oral administration of the test substances

| Compound number Comparison substance | Dose (mg/kg) | % change TC $\bar{X} \pm SD$ | TG $\bar{X} \pm SD$ |
| --- | --- | --- | --- |
| CLOFIBRAT | 100 | $-14.5 \pm 12.0$ | $-29.2 \pm 19.4$ |
| 2 | 100 | $-39.7 \pm 12.4$ | $-1.6 \pm 21.4$ |
| 3 | 100 | $-17.5 \pm 6.2$ | $-19.4 \pm 9.7$ |

2) Determination of the inhibition of cholesterol biosynthesis 3 g freshly prepared rat liver was homogenized in 6 ml ice-cooled puffer and centrifuged for 20 minutes at $20000 \times g$. The supernatant was separated off and employed for the following determinations.

To a mixture of 110 μl supernatant and 300 μl incubation solution 10 μl of the methanolic test substance solution were pipetted and incubated at 37° C. for 20 minutes. Thereafter 10 μl of an $^{14}C$-acetate solution were added by pipette and incubated for a further 30 minutes. Thereafter, to the mixture 500 μl ethanolic KOH solution were added, further incubation carried out for 60 minutes at 75° C. and thereafter the reaction stopped in an ice bath. To enable a yield correction to be made for the subsequent extraction of the $^{14}C$-cholesterol formed $^{3}H$-cholesterol (about $10^{-3}$ μCi) was added thereto by pipetting. In addition, 500 μl of an ethanolic solution of unmarked cholesterol was added. The cholesterol of the mixture was extracted twice with 1 ml petroleum ether in each case, the extract dried and taken up with 0.6 ml of an ethanol/acetone mixture (1/1). The dissolved cholesterol was then precipitated by means of 1.4 ml of a digitonin solution ($=7$ mg). After 15 h at 0° C. the precipitate was centrifuged off, dissolved with 0.5 ml methanol/glacial acetic acid (33/5) and diluted with 2 ml methanol. The radioactivity of the biosynthetically formed cholesterol was determined in 12 ml scintillation liquid (DIMILUME) by means of a scintillation counter.

Solutions used

Buffer: 6.8 g $KH_2PO_4$, 0.6 g $MgCl_2$, 0.37 g EDTA, 1.83 g nicotine amide, 51.35 g saccharose and 0.4 g mercaptoethanol were dissolved in distilled water and diluted to 500 ml ($P_H = 7.2$).

Incubation solution: The following were each individually dissolved:

8.6 mg NAD with 1.3 ml buffer
10.2 mg NADP with 1.3 ml buffer
39.6 mg glucose-6-phosphate with 0.65 ml buffer
31.6 mg glucose-6-phosphate-dehydrogenase (1000 U/0.91 ml) with 0.285 ml buffer These solutions were not mixed until immediately prior to use.

$^{14}C$-acetate:

Solution 1: 250 μCi $^{14}C$-sodium acetate in 1 ml aqua dest.

Solution 2: 512.5 mg sodium acetate in 10 ml aqua dest.

Prior to the test 0.1 ml of the solution 1 and 0.4 ml of the solution 2 were mixed and added to 2 ml aqua dest.

Ethanolic KOH: 10 g KOH were dissolved in 100 ml. ethanol

Method: R. E. Dugan et al. (Archives Biochem. Biophys. 152,21 (1972))

TABLE 3

Percentage inhibition of cholesterol biosynthesis in rat liver homogenate by the test substances

| Compound number | concentration (Mol/l) | inhibition % |
| --- | --- | --- |
| 1 | $3 \times 10^{-6}$ | 0 |
| 1 | $1 \times 10^{-5}$ | 34 |
| 1 | $3 \times 10^{-5}$ | 57 |
| 1 | $1 \times 10^{-4}$ | 68 |
| 2 | $3 \times 10^{-6}$ | 16 |
| 2 | $1 \times 10^{-5}$ | 41 |
| 2 | $3 \times 10^{-5}$ | 65 |
| 2 | $1 \times 10^{-4}$ | 75 |
| 3 | $3 \times 10^{-6}$ | 14 |
| 3 | $1 \times 10^{-5}$ | 29 |
| 3 | $3 \times 10^{-5}$ | 56 |
| 3 | $1 \times 10^{-4}$ | 70 |

(x) Percentage inhibition of the cholesterol biosynthesis compared with the blank value.

We claim:

1. P-oxybenzoic acid derivatives having the formula

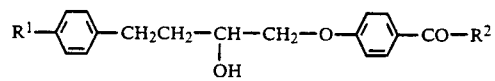

wherein:

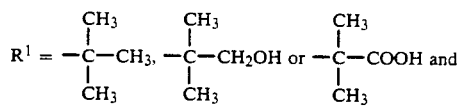

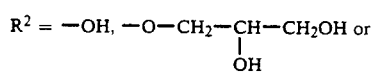

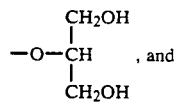, and wherein when

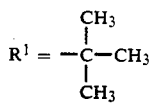

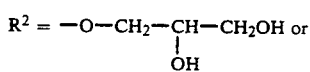

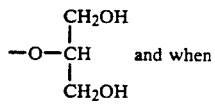 and when

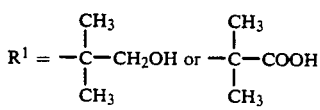

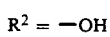

2. A p-oxybenzoic acid derivative according to claim 1 wherein

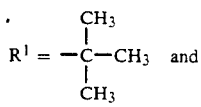

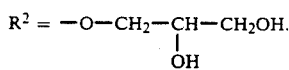

3. A p-oxybenzoic acid derivative according to claim 1 wherein

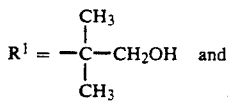

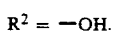

4. A p-oxybenzoic acid derivative according to claim 1 wherein

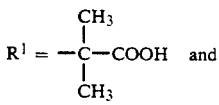

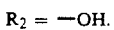

5. Process for preparation of p-oxybenzoic acid derivatives according to claim 1 comprising reacting an epoxide having the formula

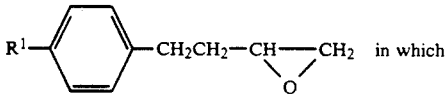

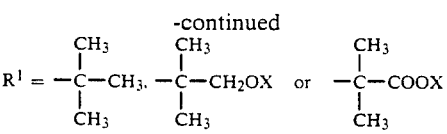

and X denotes a suitable protective group with a p-oxybenzoic acid ester having the formula

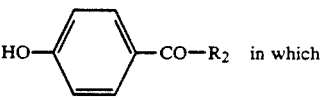

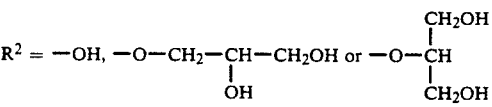

in the presence of alkali followed by removal of the protective groups wherein when

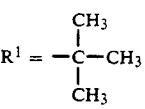

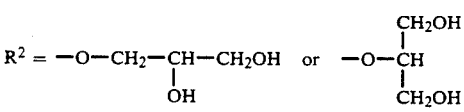

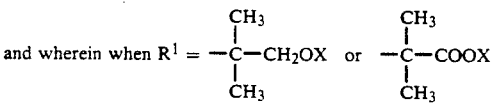

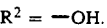

6. A process according to claim 5 wherein X is an acetyl group.

7. A pharmaceutical preparation having a hypolipemic effect comprising a p-oxybenzoic acid derivative as in claim 1.

* * * * *

UNITED STATES PATENT AND TRADEMARK OFFICE
CERTIFICATE OF CORRECTION

PATENT NO. : 5,153,353

DATED : October 6, 1992

INVENTOR(S) : Reiter et al.

It is certified that error appears in the above-identified patent and that said Letters Patent is hereby corrected as shown below:

Column 3, line 54, "hydroxybuty" should read --hydroxybutoxy --.

Column 5, line 34, "hydr oxybytoxy" should read --hydroxybutoxy -- and
Column 7, line 47, "0.4 g" should read --0.44 g --.

On the title page: Item [54] insert --NOVEL-- before "P-Oxybenzoic"

Signed and Sealed this

Twenty-sixth Day of July, 1994

Attest:

BRUCE LEHMAN

Attesting Officer    Commissioner of Patents and Trademarks